United States Patent [19]
Holland, Jr. et al.

[11] Patent Number: 6,045,596
[45] Date of Patent: Apr. 4, 2000

[54] FILTER SYSTEM TO REMOVE A CONTAMINANT FROM A FLUID STREAM

[75] Inventors: Clinton R. Holland, Jr.; Earnest R. Moehlau, both of Amherst; Christopher A. Palmerton, Clarence, all of N.Y.

[73] Assignee: Medtek Devices, Inc., Buffalo, N.Y.

[21] Appl. No.: 08/835,235

[22] Filed: Apr. 7, 1997

[51] Int. Cl.[7] .................................................. B01D 46/00
[52] U.S. Cl. .............................. 55/385.2; 55/467; 55/473
[58] Field of Search ................................ 55/385.1, 385.2, 55/467, 473, 485; 604/902, 319, 322

[56] References Cited

U.S. PATENT DOCUMENTS

| 4,082,092 | 4/1978 | Foster . | |
|---|---|---|---|
| 4,446,861 | 5/1984 | Tada . | |
| 4,487,606 | 12/1984 | Leviton et al. | 604/319 |
| 4,540,202 | 9/1985 | Amphoux . | |
| 4,541,327 | 9/1985 | Lundstrom . | |
| 4,642,128 | 2/1987 | Solorzano | 55/467 |
| 4,701,193 | 10/1987 | Roberston et al. | 55/385.1 |
| 4,906,261 | 3/1990 | Mohajer . | |
| 4,963,134 | 10/1990 | Backscheider et al. | 55/467 |
| 4,986,839 | 1/1991 | Wertz et al. | 55/467 |
| 5,226,939 | 7/1993 | Nicolas et al. | 55/467 |
| 5,242,474 | 9/1993 | Herbst et al. | 55/467 |
| 5,264,026 | 11/1993 | Paul . | |
| 5,409,551 | 4/1995 | Paul . | |
| 5,531,802 | 7/1996 | Schlor et al. | 55/467 |
| 5,597,385 | 1/1997 | Moerke | 55/473 |

*Primary Examiner*—Duane S. Smith
*Attorney, Agent, or Firm*—Phillips, Lytle, Hitchcock, Blaine & Huber

[57] ABSTRACT

The present invention is a filter system self contained within a treatment room for a medical procedure. The filter system is partially incorporated into a standard surgical arm. The filter is mounted on the control unit of the surgical arm, which is at the free end of the surgical arm. A vacuum device to create airflow through the filter is located distant from the filter, but still within the treatment room. The vacuum device is adapted to exhaust either into a portion of the treatment or the HVAC system of the facility in which the treatment room resides. Controls for the filter system are also incorporated into the control unit of the surgical arm.

7 Claims, 4 Drawing Sheets

FILTER SYSTEM TO REMOVE A CONTAMINANT FROM A FLUID STREAM

TECHNICAL FIELD

The present invention relates generally to self-contained filter systems, and more particularly, to self-contained filter systems used to remove contaminants from a fluid stream generated by medical procedures including surgical procedures.

BACKGROUND

Many surgical instruments used in modern medical procedures generate smoke plumes as a by-product. Examples of such surgical instruments are lasers, electrosurgical units, laproscopes, drills and ultrasonic devices. Additionally, chemical mixes used in medical procedures can generate hazardous vapors also categorized as smoke plumes.

Many times the smoke plume from a medical procedure has a distinct and unpleasant odor. Accordingly, it is desirable to remove the smoke plume for the convenience of the staff.

However, health concerns raise a more significant reason to remove smoke plumes. It is known that smoke plumes can carry active particles such as viruses, bacteria mycobacteria and other microbes. These particles may be transmitted to the staff performing the medical procedure through contact with the plume. Furthermore, these particles can remain suspended in the operating room thus exposing the next patient or surgical staff. Examples of active particles known to exist in some smoke plumes are mycobacterium tuberculosis, condylomata acuminata, human immunodeficiency virus DNA, and human papilloma virus DNA.

Recently, government agencies have begun to investigate smoke plumes and advise the removal or filtering of smoke plumes generated by laser surgery. See "OSHA Technical Manual—Section V—Chapter 1 Appendix V:1–3, Physical Agents", "OSHA Technical Manual—Section V—Chapter 1, Hospital Investigations: Health Hazards" and "Health Hazard Information Bulletin: Hazards of Laser Surgery Smoke", Apr. 11, 1988. This concern has extended to other procedures generating smoke plumes such as electrosurgery. See "Standard Interpretations and Compliance Letters—Hazards of Smoke Generated from Surgical Procedures" at http://www.osha-slc.gov. Furthermore, the "1996 Standard & Recommended Practices" issued by the Association of Operation Room Nurses, Inc. recommends removal of smoke plumes during electrosurgical procedures, and the Center for Disease Control and Prevention (CDC) and the National Institute for Occupational Safety and Health (NIOSH) issued in Sep. of 1996 issued a Hazard Control II (HCII) entitled "Control of Smoke from Laser/Electric Surgical Procedures" similarly recommending removal of smoke plumes generated by electrosurgery.

Three methods are known to control smoke plumes: centralized vacuum/local filter, local vacuum/local filter and centralized vacuum/centralized filter unit.

Centralized vacuum systems have been used in health care facilities for decades. A central vacuum is connected to a duct system extending throughout the facility. The duct system terminates at a number of wall outlets in a plurality of procedure rooms. These units are designed to remove fluids and small particles generated by medical procedures (e.g., blood and bone chips).

The first response by the industry to address the identified hazards of smoke plumes was to adapt the known centralized vacuum systems into centralized vacuum/local filter systems capable of filtering smoke plumes. A centralized vacuum/local filter system generally comprises the existing centralized vacuum system, two lengths of flexible tubing and a local filter. One end of the first length of flexible tubing is connected to the centralized vacuum system wall outlet. The other end of the first section of tubing is connected to the exhaust of a local filter. One end of the second section of flexible tubing is connected to the inlet end of the local filter, and the other end of the second section of flexible tubing is then positioned adjacent the location of the smoke plume. The suction created by the central vacuum draws the smoke plume sequentially through the first flexible tubing section, the local filter, the second flexible tubing section and the duct work of the centralized vacuum system.

Centralized vacuum/local filter systems have deficiencies. The vacuum power generated is limited by the preexisting central vacuum. Some filters are difficult to use as central vacuums were not developed to create a pressure drop across robust filters. Accordingly, the efficiency of the filtration is limited by the types of filters that can be used.

Local vacuum/local filter systems were developed next. These generally comprise a portable housing, having a filter and local vacuum, and a length of flexible tubing connected at one end to the filter inlet and its other end adapted to be located adjacent the smoke plume. The local vacuum sequentially draws the smoke plume through the flexible tubing and the filter. Local vacuum/local filter systems have many positive features including a comparable low cost, portability for use between rooms on an as-needed basis, ease of filter replacement, flexibility to use various filters having desired characteristics, and restriction of contamination to the disposable flexible tubing, and the disposable filter. However, local vacuum/local filter systems have not been the final answer as they also have significant drawbacks. Most local vacuum/local filter systems use local vacuums which generate significant noise. Most local vacuum/local filter systems occupy valuable floor space, and associated power cords and tubing may drape onto the floor creating a hazard. Finally, local vacuum/local filter systems generally recirculate the filtered air back into the treatment room.

Recently, centralized vacuum/centralized filter systems have been developed in an attempt to address the problems presented by local vacuum/local filter systems. An example of a centralized vacuum/centralized filter system is described in U.S. Pat. Nos. 5,264,026 and 5,409,551, both to Paul and both entitled CENTRALIZED LASER PLUME EVACUATION SYSTEM THROUGH ARTICULATING ARMS. The centralized vacuum/centralized filter systems are best described as a modification to the known centralized vacuum/local filter systems. The centralized vacuum/centralized filter system generally comprises a central vacuum, usually located in the basement of a health care facility, a central filter downstream from the central vacuum, a centrifugal separation tank upstream from the central vacuum, and duct work extending throughout the health care facility connecting to the centrifugal separation tank. It is known to connect the duct work of the centralized vacuum/centralized filter system to tubing running within an articulating arm mounted within a treatment room, the tubing ending at an outlet on the arm control panel. A disposable flexible tube is connected at one end to the outlet on the arm control panel with its other end adapted to be located adjacent the smoke plume. The central vacuum draws a smoke plume sequentially through the disposable tubing, the arm tubing, the duct work, and the centrifugal separation tank. The central vacuum then exhausts the smoke plume through the central filter where contaminants are removed.

The centralized vacuum/centralized filter system as described occupies no floor space, eliminates associated cords and tubing from the floor and reduces noise in the operating room by placing the central vacuum at a distant location. However, centralized vacuum/centralized filter systems have significant draw-backs. Centralized vacuum/centralized filter systems are expensive both to install and to operate on a per procedure basis. Extensive duct work and tubing must be run throughout the health care facility, and a large, high powered central vacuum must be used to provide the necessary suction. In addition, repair can be difficult as the majority of the duct work is normally in service areas above ceiling or within floors. Furthermore, the central filter does not allow selective use of filters having desired characteristics for certain procedures. A significant amount of energy must be used to maintain the vacuum throughout the extensive duct work. Most importantly, as the central filter is placed after the central vacuum, all interior surfaces of the arm tubing, duct work, centrifugal separation tank and vacuum unit are exposed to the contaminated smoke plume. The '026 and '511 patents suggest frequent introduction of a liquid disinfectant/antimicrobial solution into the arm tubing and duct work to address this concern. However, it is questionable whether this procedure would be effective absent the complete flushing of the arm tubing and duct work, especially at bends and incongruities of the arm tubing and duct work where particulate is most likely to collect. Finally, the centralized vacuum/centralized filter system are inappropriate to install in smaller facilities such as individual physician's offices, surgi centers, clinics and ambulatory centers.

Accordingly, it would be useful to have a filter system for a contaminated fluid stream that does occupy floor space, does not drape power cords and tubing on the floor, is quiet but provides a powerful vacuum, allows for the easy replacement of filters, is inexpensive to install and use, and where only disposable portions of the system come in contact with the smoke plume when contaminated.

BRIEF DESCRIPTION OF THE INVENTION

With reference to corresponding parts and portions for purposes of illustration and not be means of limitation, a filter system adapted to remove a contaminant from a fluid stream generated by a source within an enclosure is disclosed. The filter systems includes an arm within the enclosure mounted on the enclosure having a free end adapted to be moved adjacent the source of the contaminated fluid stream. The filter system further includes a filter mounted on the arm. The filter has an inlet and an outlet. The filter system further includes a first tube having first and second ends where the first tube first end is adapted to be disposed adjacent the source of the contaminated fluid stream and the first tube second end is connected to the filter inlet. The filter system also includes a vacuum means for creating a pressure differential. The vacuum means has an inlet and an outlet and is within the enclosure. The filter system also includes a second tube having first and second ends. The first end of the second tube is connected to the filter outlet, the second tube runs along the arm, and the second end of the second tube is connected to the inlet of the vacuum means. The vacuum means may draw the fluid stream sequentially from its source, through the first tube, the filter and the second tube, and may exhaust the fluid stream through the vacuum means.

An object of the invention is to provide a filter system for a contaminated fluid stream wherein all portions are contained within the enclosure having the source of the fluid stream.

Another object of the invention is to provide a filter system which is a low cost alternative to centralized vacuum/centralized filter systems.

Another object of the invention is to provide a filter system where only disposable portions of the filter system are exposed to the contaminated fluid stream.

Another object of the invention is to provide a filter system that does not occupy valuable floor space, or exhaust the fluid stream back into the enclosure or have cords or tubing draped on the floor of the enclosure.

Another object of the invention is to provide a low noise filter system.

Still another object of the invention is to provide a filter system integrated with articulated arms commonly installed in treatment rooms.

DESCRIPTION OF THE PREFERRED EMBODIMENTS

Figure 1:
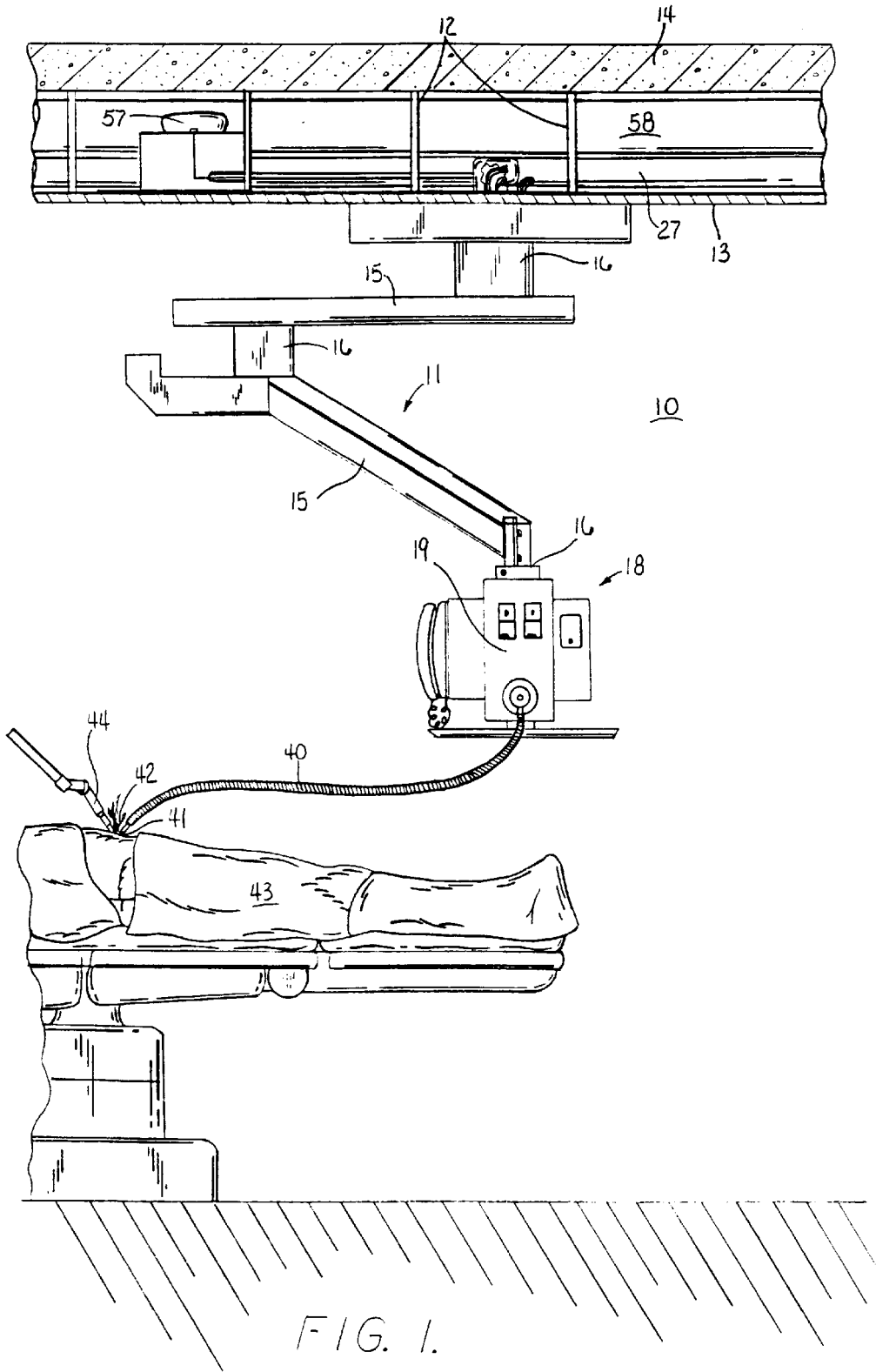
FIG. 1 is a fragmentary view, partially in section, of a treatment room having a standard surgical arm and the filter system of the present invention.

At the outset, it should be clearly understood that like reference numerals are intended to identify the same structural elements, portions or surfaces consistently throughout the several drawing figures, as such element, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.) simply refer to the orientation of the illustrated structure as the particular drawing figure faces the reader. Similarly, the terms "inwardly"and "outwardly" generally refer to the orientation of a surface relative to its axis of elongation, or axis of rotation, as appropriate.

FIG. 1 shows a portion of a treatment room 10 having a standard surgical arm 11 and the filter system of the present invention. Treatment room 10 is a surgical operatory in a hospital, but arms used in any treatment environment can incorporate the filter system of the present invention. Examples are arms used in individual physician offices, surgi centers, clinics and ambulatory centers. One end of arm 11 is fixedly mounted to structural ceiling 14 by rods, severally indicated at 12 which pass through finished ceiling 13. Structural ceiling 14 is a portion of the concrete structural frame of the hospital. Arm 11 comprises a series of hollow arm portions, severally indicated at 15, and hollow elbows, severally indicated at 16, terminating at the free end having a service unit 18.

Figure 2:
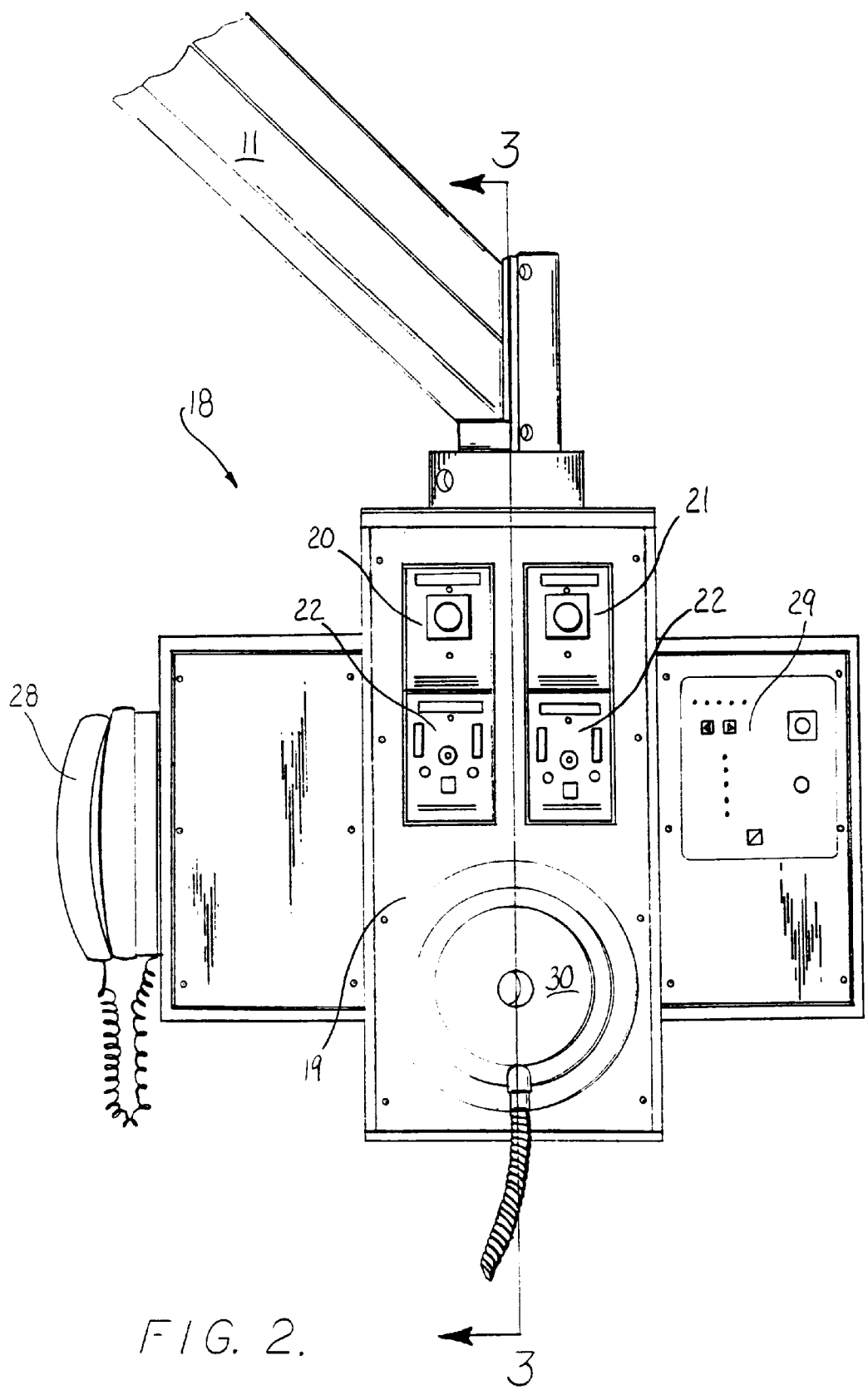
FIG. 2 is a front elevation of the service unit of a surgical arm.
Figure 5:
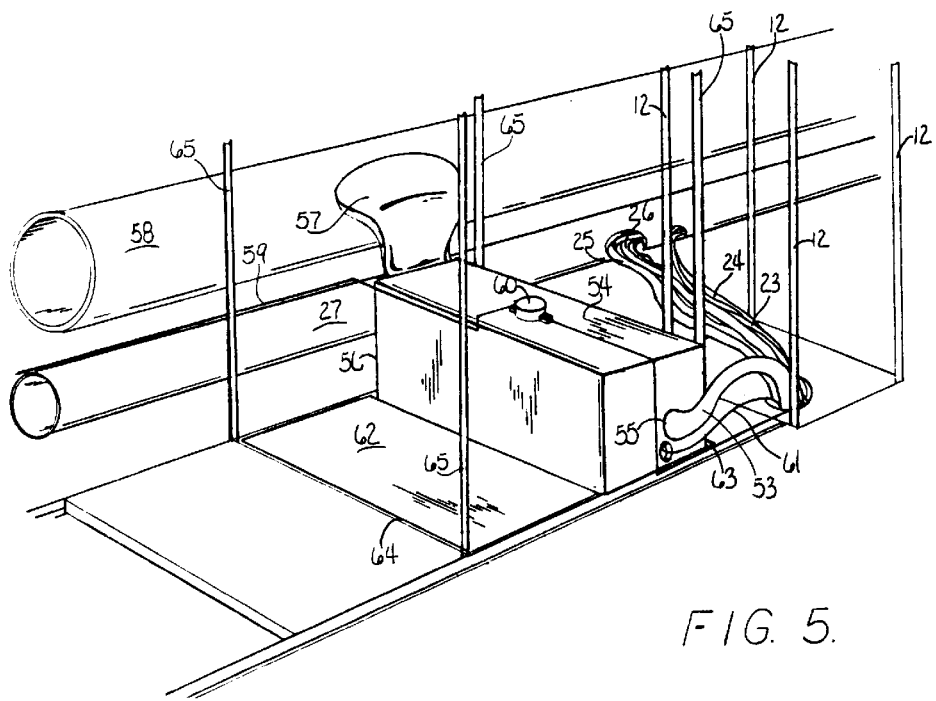
FIG. 5 is a perspective view of the treatment room above finished ceiling 13.

Service unit 18 includes a control panel 19 having outlets and controls for desired capabilities and functionality. For example, FIG. 2 shows service unit 18 and its control panel 19. On control panel 19 are gas delivery outlets to deliver carbon dioxide 20 and nitrogen 21, as well as two vacuum outlets, severally indicated at 22. Adverting to FIG. 3, gas delivery outlet 20 is connected to tube 23, and vacuum outlet 22 is connected to tube 25 within service unit 18. Similarly, gas delivery outlet 21 is connected to tube 24, and vacuum outlet 22 below gas delivery outlet 21 is connected to tube 26 within service unit 18. As best seen in FIGS. 1 and 5, tubes 23–26 run through hollow arm portions 15 and elbows 16 and into a centralized gas delivery and centralized vacuum system 27. Service unit 18 also includes amenities such as a telephone 28 as well as filter control panel 29, discussed in greater detail below.

Figure 3:
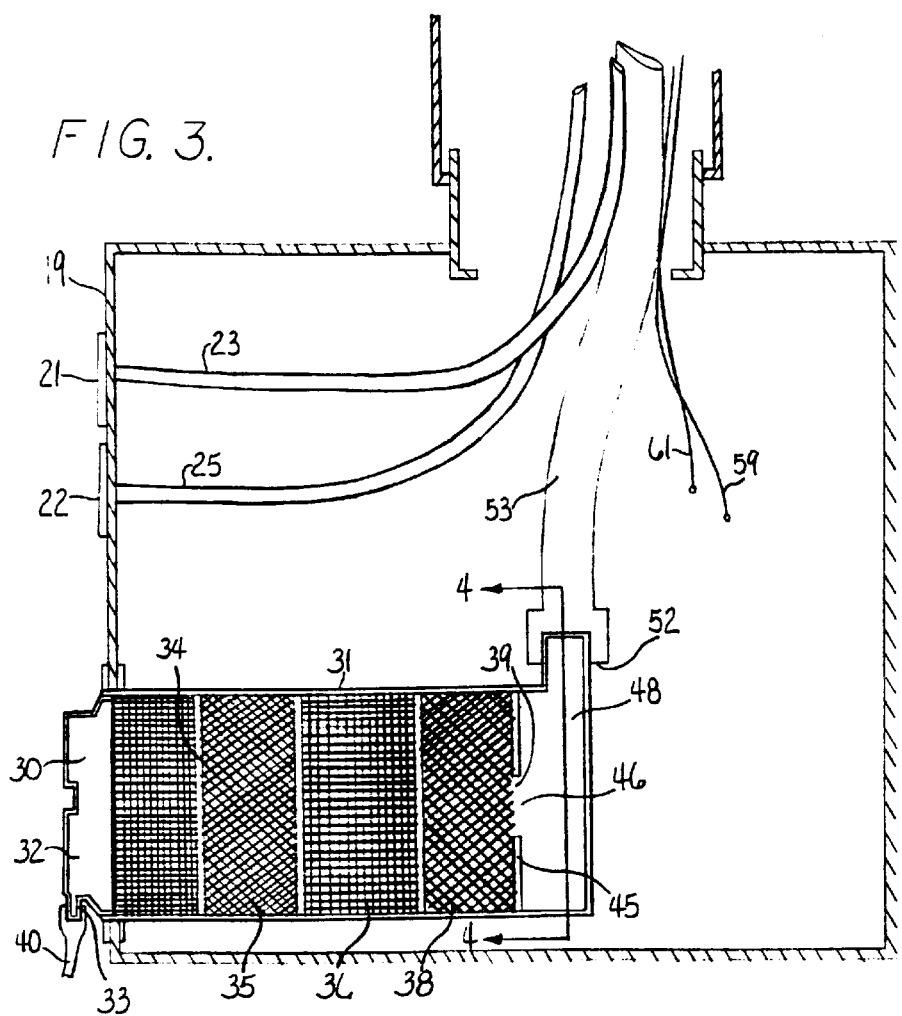
FIG. 3 is a fragmentary cross section of FIG. 2 along line 3—3.
Figure 4:
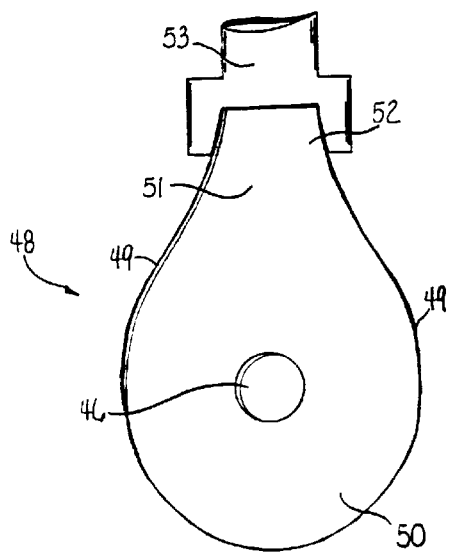
FIG. 4 is a fragmentary cross section of FIG. 3 along line 4—4.

As shown in FIGS. 3 and 4, filter 30 is operably positioned within a sleeve 31 mounted on service unit 18. Filter 30 here is a Buffalo Filter[198] ViroSafe® filter available from Buffalo Filter of 6000 North Bailey Avenue, Amherst, N.Y. 14228. Filter 30 is a high efficiency style filter including a molded cover 32 having an inlet 33, filter material in four portions 34, 35, 36 and 38, and an outlet 39. Inlet 33 is configured to sealably mate with a disposable tube 40. Threaded and friction connections are examples of connections that can be used to sealably connect tube 40 with inlet 33. Tube 40 is traditionally made of a flexible plastic such as polyvinyl chloride or polypropelyene. Common diameters for tube 40 are ¼", ⅞" and 1¼". Tube 40 can be any length. However, a length of at least 6' has been found to be useful in most situations. Adverting to FIG. 1, the free end of tube 40 is maneuvered to be adjacent the source 41 of a smoke plume 42. Source 41 in this case is a medical procedure performed on a patient 43 using a laser device 44. Smoke plumes may also be produced by electrosurgical devices, orthopedic instruments (e.g., saws, augers or drills), ultrasonic/harmonic scalpels, chemical mixes (e.g., bone cement) and minimally invasive surgical procedures (e.g., laproscopic or endoscopic procedures).

Filter 30 has four distinct portions. Filter portion 34 is a gross particulate filter adapted to remove large particulate on the order of 0.5 micrometers or greater. Filter portion 35 is an Ultra Low Penetration Air (ULPA) filter which captures particulate and microbes of 0.01 micrometers or greater with an efficiency of 99.99995% removal. Filter portion 36 is an activated carbon bed, including fines, adapted to primarily remove odor or toxins suspended in a smoke plume. Filter portion 38 is a gross particulate filter designed primarily as a barrier inhabiting migration of the carbon bed fines of filter portion 36.

It is known to provide filter portion 35 with antimicrobial properties by coating the exterior of the strands comprising filter portion 35 with an antimicrobial (See U.S. Pat. No. 4,906,261 to Mohajer, the disclosure of which is hereby incorporated by reference) or by embedding homogeneously throughout each strand comprising filter portion 35 an antimicrobial (See U.S. patent application Ser. No. 08/221, 552 to Holland, abandoned in favor of continuing U.S. patent application Ser. No. 08/827,925, now U.S. Pat. No. 5,874,052, the disclosure of which is hereby incorporated by reference).

Filter 30 snugly fits within a cylindrical sleeve 31 extending from control panel 19 into service unit 18. The base 45 of sleeve 31 includes an opening 46 that registers with outlet 39 of filter 30. Attached to base 45 of sleeve 31 is a plenum chamber 48. As best seen in FIG. 4, plenum chamber 48 is generally tear-shaped having a side wall 49 defining a body portion 50 adjacent opening 46, and a neck portion 51 above body portion 50. Neck portion 51 ends at an exhaust 52. Exhaust 52 typically has a diameter 1¼" or 1½", but can vary depending on the needs of the filter system of the present invention. A second tube 53 is sealably connected to exhaust 52. Threaded and friction connections are examples of connections that can be used to sealably connect tube 53 to exhaust 52. Tube 53 is typically 1¼" in diameter, but can vary depending on the needs of filter system of the present invention.

Tube 53 extends upward within arm 11. However, tube 53 could be secured to the exterior of arm 11. Adverting now to FIGS. 1 and 5, tube 53 continues above finished ceiling 13 where it connects to a vacuum device 54 at its inlet 55. Here, vacuum device 54 includes a backward curve three-stage motor made by Ametek Corporation, Lamb Electric Division which operates a fan blade to generate a pressure differential along tube 53, plenum 48, filter 30 and tube 40. The exhaust 56 of vacuum device 54 leads into a passageway 57 connecting vacuum device 54 to the HVAC duct work 58 of the hospital. Accordingly, even if trace amounts of contaminants are present in the exhaust of vacuum device 54, they are transported away from treatment room 10 to minimize the exposure to the staff. It is possible, however, to exhaust vacuum device 54 directly into the space between finished ceiling 13 and structural ceiling 14 by removing passageway 57.

The use of plenum chamber 48 greatly enhances the efficiency and power of the filter system of the present invention as compared to connecting second tube 53 directly about opening 46. The use of plenum chamber 48 increases the flow rate up to 10% as compared to connecting second tube 53 directly about opening 46. Accordingly, vacuum device 54 can operate at a lower power setting and still provide the desired flow rate, in turn reducing the noise generated by vacuum device 54 and reducing the energy consumed by vacuum device 54.

As seen in FIGS. 3 and 5, A/C power wire 59 connects to junction 60 on vacuum device 54, proceeds through arm 11 and terminates at control panel 28. Power wire 59 provides power to vacuum device 54 and filter control panel 29. Control wire 61 connects filter control panel 29 to vacuum device 54 and transfers control signals from filter control panel 29 to vacuum device 54.

Vacuum device 54 is mounted on a metal access panel 62 which is rotatably mounted by a hinge 63 to a metal frame 64 suspended from ceiling 14 by rods, severally indicated at 65. Vacuum device 54, access panel 62, passageway 57, second tube 53, power wire 59 and control wire 61 are adapted to allow access panel 62 to open into treatment room 10 for easy repair and maintenance of vacuum device 54.

Figure 6:
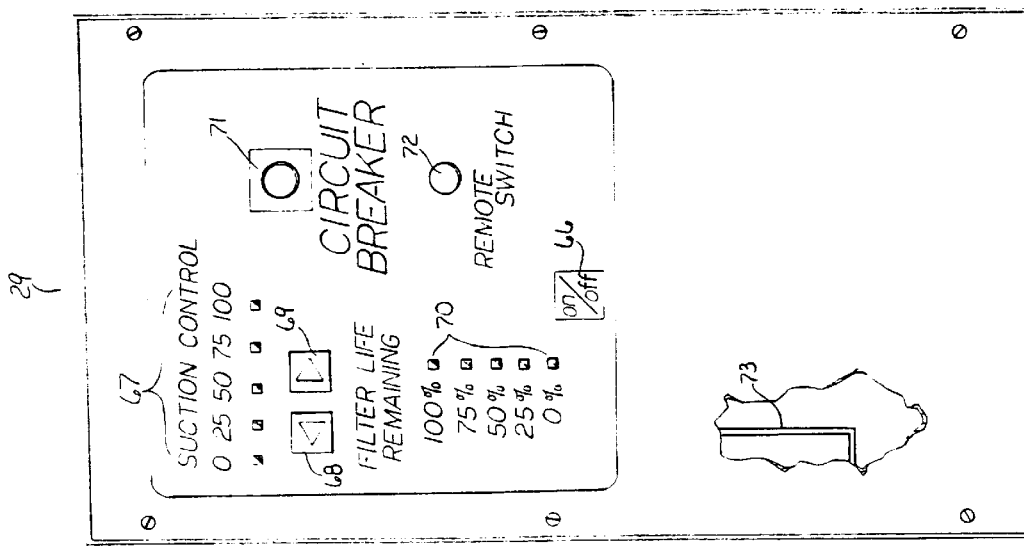
FIG. 6 is a front elevation of control panel 28.

Vacuum device 54 is controlled by filter control panel 29. As best seen in FIG. 6, filter control panel 29 includes an on/off switch 66, a suction control indicator 67, suction controls 68 and 69, filter life indicator 70, circuit breaker 71, remote switch port 72, and filter life timer 73. A first press of on/off switch 66 activates vacuum device 54 and filter life timer 73. A second press of on/off switch 66 deactivates vacuum device 54 and filter life timer 73. Each filter 30 has a life span, traditionally measured in hours of operation. Here, filter 30 has an eight hour operation life span. Filter life timer 73 is reset each time a new filter 30 is inserted into sleeve 31. Thereafter, each time on/off switch 65 activates vacuum device 54, filter life timer 73 is also activated, and cumulatively records the amount of time filter 30 has been in operation. Filter life timer 73 compares the cumulative operation time of filter 30 to its life span to determine the percentage of filter life remaining, which is displayed on filter life indicator 70. Filter life indicator 70 here is a series of lights, each light corresponding to percentage value of filter life printed on the face of control panel 28. For example, filter 30 has a life span of eight hours. If filter 30 is operated for four hours, filter life timer 73 will light the lowest three lights of filter life indicator 70 to indicate filter 30 has 50% of its filter life remaining. Other filter life indicators can be used, such as an LCD display.

Airflow through filter 30 can be controlled at filter control panel 29 through suction control 68 and 69. This control system is different from the prior art suction airflow is controlled by a ball valve in the airflow pathway. (See FIG. 6 of U.S. Pat. No. 5,264,026 to Paul). Such control systems are necessary in centralized section systems as the speed of the central vacuum cannot be remotely altered. Toggling switch 68 reduces airflow toward a nearly zero cubic feet per minute (CFM) minimum. Toggling switch 69 will increase suction airflow toward a 80–90 CFM minimum. Airflow also depends on the diameter of tube 40. The diameter of tube 40 sets the upper limit of airflow. The following chart sets forth the upper limits for popular diameters of tubes 40 in the system described herein:

| Diameter | Maximum Suction Airflow |
|---|---|
| 1/4" | 4–5 CFM |
| 7/8" | 40–50 CFM |
| 1 1/4" | 80–90 CFM |

Circuit breaker 71 is rated at 15 amps and will interrupt the flow of current to vacuum device 54 when tripped. Again placing circuit breaker 71 on filter control panel 29 allows for easy, local resetting if circuit breaker 71 trips.

It is also known to control filter systems using remote control systems such as foot switches and radio frequency sensors. (See U.S. Pat. No. 5,318,516 to Cosmescu, the disclosure of which is hereby incorporated by reference). Remote switch port 72 is adapted to accommodate these remote control systems.

The filter system of the present invention operates as follows. Before the start of the medical procedure, the medical staff chooses a filter 30 having desired characteristics and inserts the filter into sleeve 31. It is possible the medical staff will choose to use the filter currently in sleeve 31. A remote control system, if any, is plugged into remote switch port 72. Finally, a tube 40 having desired characteristics of length and diameter is connected to filter inlet 33. The filter system is now ready for operation. The medical staff begins the medical procedure on patient 43. Vacuum device 54 is toggled on by pressing on/off switch 66, airflow is adjusted using switches 68 and 69, and the free end of tube 40 is positioned adjacent source 41. As smoke plume 42 is generated by operation of laser device 44, smoke plume 42 is drawn into tube 40, through filter 30 where desired contaminants are removed, through plenum chamber 48, through second tube 53, through vacuum device 54, and exhausted through passageway 57 into HVAC duct work 58. Importantly, contaminants are removed before smoke plume 42 reaches any portion of the filter system of the present invention that is not disposable.

Modifications

While the invention is described in terms of preferred embodiments thereof, one of ordinary skill in the art will readily appreciate the various modifications and changes may be made to the invention without departing from the concepts illustrated by the specification, drawings and append claims.

In particular, various types of filters may be used depending on the needs of the medical procedure performed. In addition, a scavenger unit could be connected to service unit 18 to filter fluids and large particulate drawn through tube 40 before reaching filter 30. Also, surgical booms need not be connected to a ceiling, but could be connected to a wall or the floor.

These and other modifications would be apparent to one of ordinary skill in the art and accordingly, the invention should be read to include these modifications.

We claim:

1. A filter system adapted to remove a contaminant from a fluid stream generated by a source within an enclosure, comprising:

an arm within said enclosure having one end mounted on the enclosure and having a free end adapted to be moved adjacent the source;

a filter mounted on said arm, said filter having an inlet and an outlet;

a first tube having first and second ends, said first tube first end adapted to be disposed adjacent the source, said first tube second end connected to said filter inlet;

a vacuum means for creating a pressure differential mounted within the enclosure, said vacuum means having an inlet and an outlet;

a second tube having first and second ends, said second tube first end connected to said filter outlet, said second tube running along said arm, and said second tube second end connected to said vacuum means inlet;

said enclosure being a treatment room comprising structural walls, a structural ceiling, and a structural floor;

said treatment room also comprising a finished ceiling, and a ceiling volume defined by said finished ceiling, said structural ceiling, and said structural walls; and said vacuum means mounted to said finished ceiling and within said ceiling volume;

whereby said vacuum means may draw the fluid stream sequentially through said first tube, said filter and said second tube, and may exhaust said fluid stream through said vacuum means.

2. The filter system as set forth in claim 1 further comprising a passageway connecting said vacuum means exhaust to the HVAC system servicing the treatment room;

whereby said vacuum means exhausts said fluid stream sequentially through said vacuum means exhaust and said passageway into said HVAC system.

3. A filter system adapted to remove a contaminant from a fluid stream generated by a source within an enclosure, comprising:

an arm within said enclosure having one end mounted on the enclosure and having a free end adapted to be moved adjacent the source;

a filter mounted on said arm, said filter having an inlet and an outlet;

said filter having antimicrobial characteristics;

a first tube having first and second ends, said first tube first end adapted to be disposed adjacent the source, said first tube second end connected to said filter inlet;

a vacuum means for creating a pressure differential mounted within the enclosure, said vacuum means having an inlet and an outlet;

a second tube having first and second ends, said second tube first end connected to said filter outlet, said second tube running along said arm, and said second tube second end connected to said vacuum means inlet;

whereby said vacuum means may draw the fluid stream sequentially through said first tube, said filter, and said second tube, and may exhaust said fluid stream through said vacuum means.

4. A filter system adapted to remove a contaminant from a fluid stream generated by a source within an enclosure, comprising:

an arm within said enclosure having one end mounted on the enclosure and having a free end adapted to be moved adjacent the source;

a filter mounted on said arm, said filter having an inlet and an outlet;

a first tube having first and second ends, said first tube first end adapted to be disposed adjacent the source, said first tube second end connected to said filter inlet;

a vacuum means for creating a pressure differential mounted within the enclosure, said vacuum means having an inlet and an outlet;

a second tube having first and second ends, said second tube first end connected to said filter outlet, said second tube running along said arm, and said second tube second end connected to said vacuum means inlet;

said enclosure comprising a structural wall;

said arm mounted on said structural wall;

whereby said vacuum means may draw the fluid stream sequentially through said first tube, said filter, and said second tube, and may exhaust said fluid stream through said vacuum means.

5. A filter system adapted to remove a contaminant from a fluid stream generated by a source within an enclosure, comprising:

an arm within said enclosure having one end mounted on the enclosure and having a free end adapted to be moved adjacent the source;

a filter mounted on said arm, said filter having an inlet and an outlet;

a first tube having first and second ends, said first tube first end adapted to be disposed adjacent the source, said first tube second end connected to said filter inlet;

a vacuum means for creating a pressure differential mounted within the enclosure, said vacuum means having an inlet and an outlet;

a second tube having first and second ends, said second tube first end connected to said filter outlet, said second tube running along said arm, and said second tube second end connected to said vacuum means inlet;

said arm including a service unit;

said service unit including a filter sleeve;

said filter mounted within said filter sleeve;

whereby said vacuum means may draw the fluid stream sequentially through said first tube, said filter, and said second tube, and may exhaust said fluid stream through said vacuum means.

6. The filter system as set forth in claim 5 wherein said filter sleeve comprises a wall defining a filter volume corresponding to the shape of said filter, and a base defining a plenum chamber, and an opening for communication between said filter volume and said plenum chamber; and said plenum chamber includes a body and a neck, said opening in communication with said plenum chamber body, and said second tube first end connected to said neck.

7. The filter system as set forth in claim 5 wherein said body has a substantially greater volume than said neck.

* * * * *